US012178962B2

(12) United States Patent
McCarthy et al.

(10) Patent No.: US 12,178,962 B2
(45) Date of Patent: Dec. 31, 2024

(54) AUTOMATIC RESCUE BREATHING UNIT WITH KEYING SYSTEM

(71) Applicants: Daniel A. McCarthy, Tyler, TX (US); Liana Al-Natour, Richardson, TX (US); Khang Vo, Garland, TX (US); Hersh Singh, Richardson, TX (US); Khushi Ashish Shah, Richardson, TX (US); Carlos Paclibar, Frisco, TX (US)

(72) Inventors: Daniel A. McCarthy, Tyler, TX (US); Liana Al-Natour, Richardson, TX (US); Khang Vo, Garland, TX (US); Hersh Singh, Richardson, TX (US); Khushi Ashish Shah, Richardson, TX (US); Carlos Paclibar, Frisco, TX (US)

( * ) Notice: Subject to any disclaimer, the term of this patent is extended or adjusted under 35 U.S.C. 154(b) by 0 days.

(21) Appl. No.: 18/525,346

(22) Filed: Nov. 30, 2023

(65) Prior Publication Data
US 2024/0189532 A1    Jun. 13, 2024

Related U.S. Application Data

(60) Provisional application No. 63/386,435, filed on Dec. 7, 2022.

(51) Int. Cl.
*A61M 16/10*    (2006.01)
*A61M 16/20*    (2006.01)

(52) U.S. Cl.
CPC ...... *A61M 16/1005* (2014.02); *A61M 16/201* (2014.02)

(58) Field of Classification Search
CPC .............. A61M 16/0833; A61M 16/00; A61M 16/0816; A61M 16/0875; A61M 2205/6009; A61M 2205/6045; A61B 2563/226
See application file for complete search history.

(56) References Cited

U.S. PATENT DOCUMENTS

| 5,944,013 | A | 8/1999 | Burch |
| 2005/0085799 | A1 | 4/2005 | Luria et al. |
| 2005/0092324 | A1 | 5/2005 | Bowden et al. |
| 2011/0247623 | A1 | 10/2011 | McCarthy |

OTHER PUBLICATIONS

International Search Report and Written Opinion for International Application No. PCT/US2023/081941, date mailed May 1, 2024, 15 pgs.

*Primary Examiner* — Margaret M Luarca
(74) *Attorney, Agent, or Firm* — Kowert, Hood, Munyon, Rankin & Goetzel, P.C.; Gareth M. Sampson

(57) ABSTRACT

A rescue breathing apparatus is disclosed. The apparatus is an automatic rescue breathing unit (ARBU) device that includes two sub-systems—an airway device keying mechanism and a ventilation unit. The keying mechanism may trigger and determine breath profile and parameters delivered by the ventilation unit. The ARBU device may connect to an air/oxygen source via a pressure regulator. The ARBU device may include a manifold, a keying chamber, an adult channel for providing breath to adult patients, a child channel for providing breath to child patients, and an infant channel for providing breath to infant patients. The ARBU device may also include a constant flow channel.

20 Claims, 13 Drawing Sheets

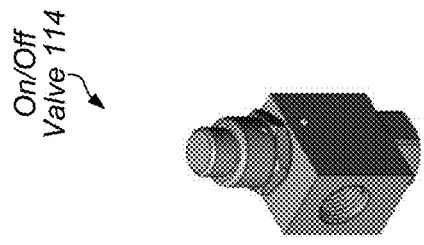
FIG. 6
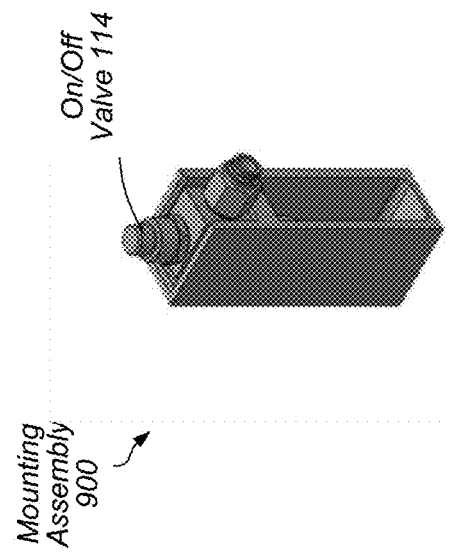
FIG. 7A
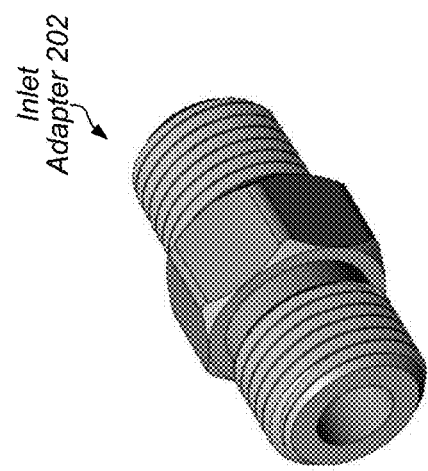
FIG. 7
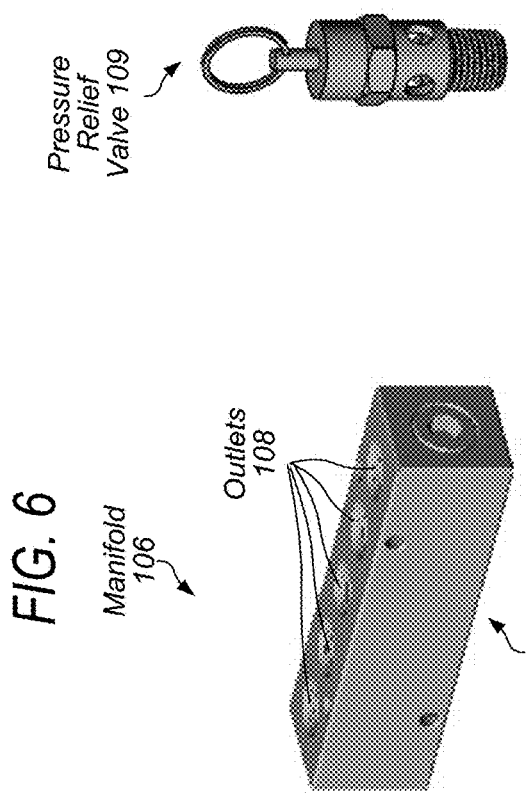
FIG. 8
FIG. 9

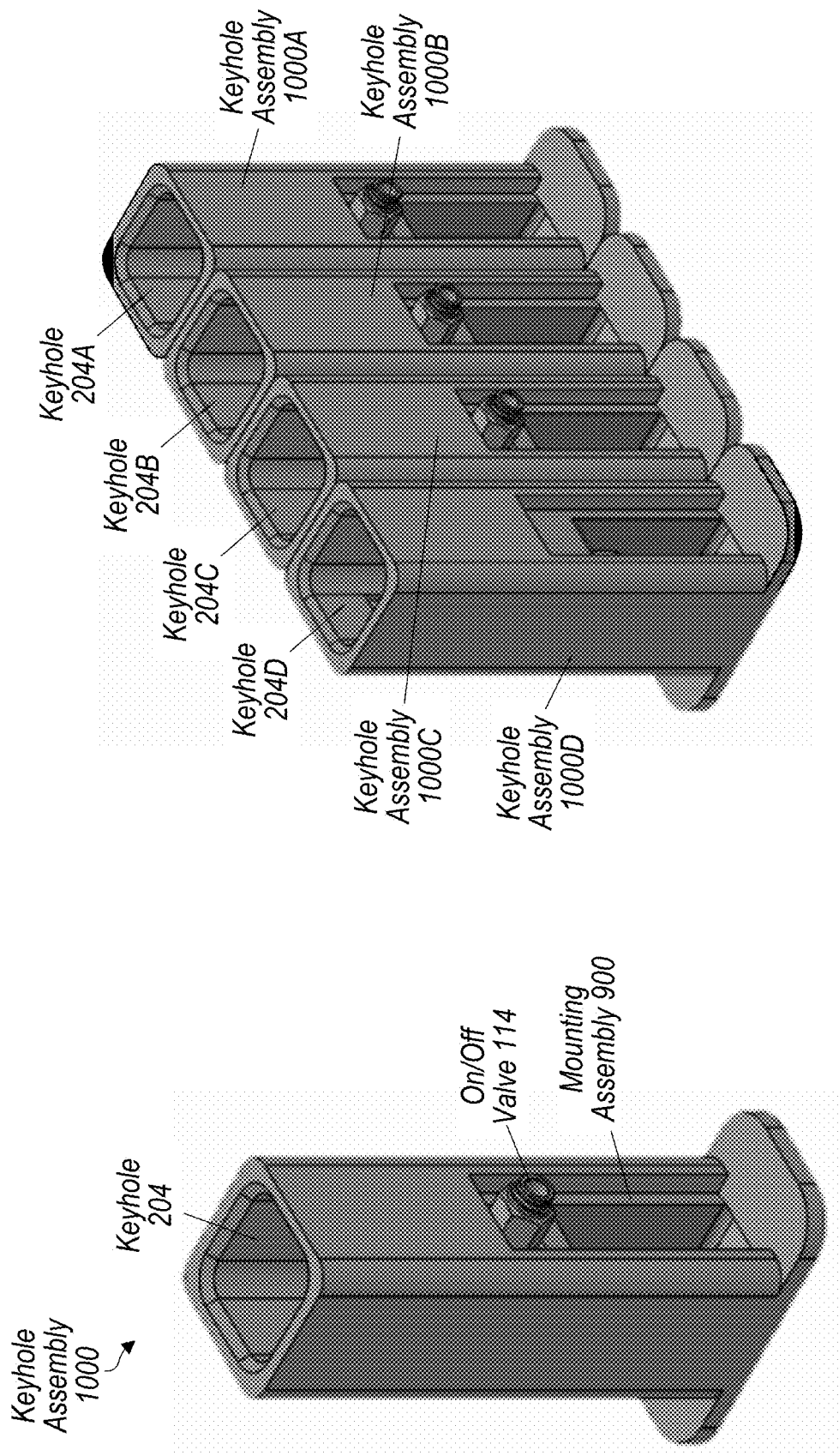

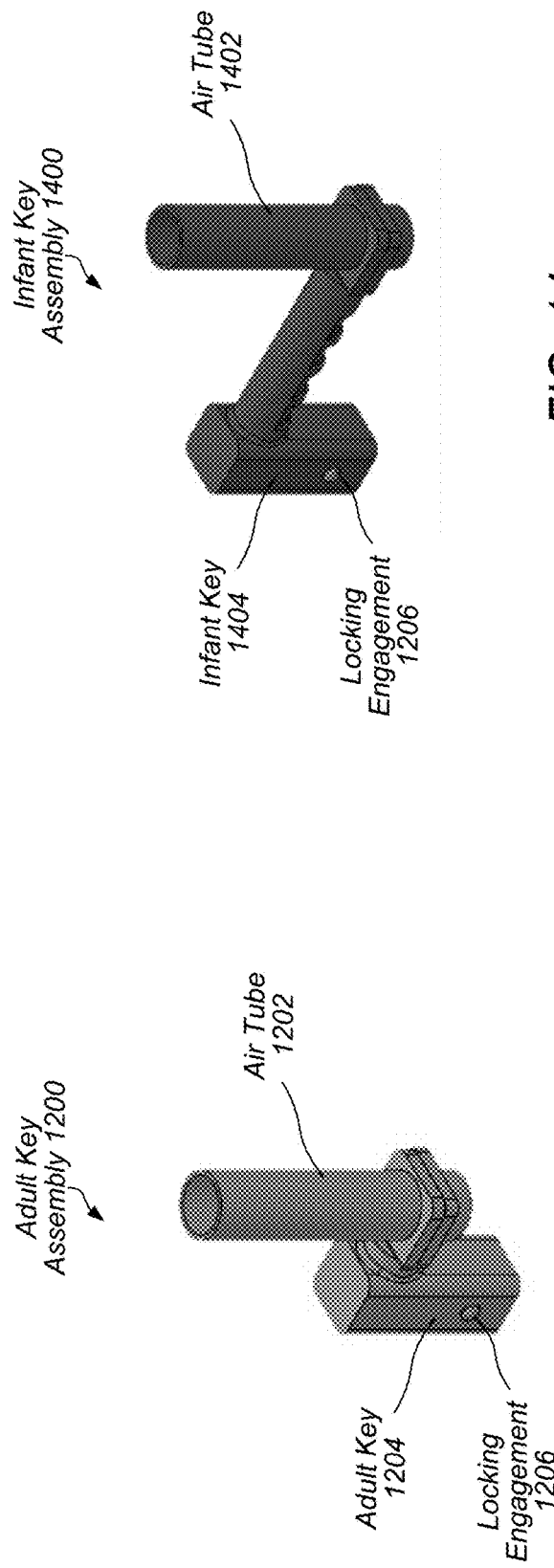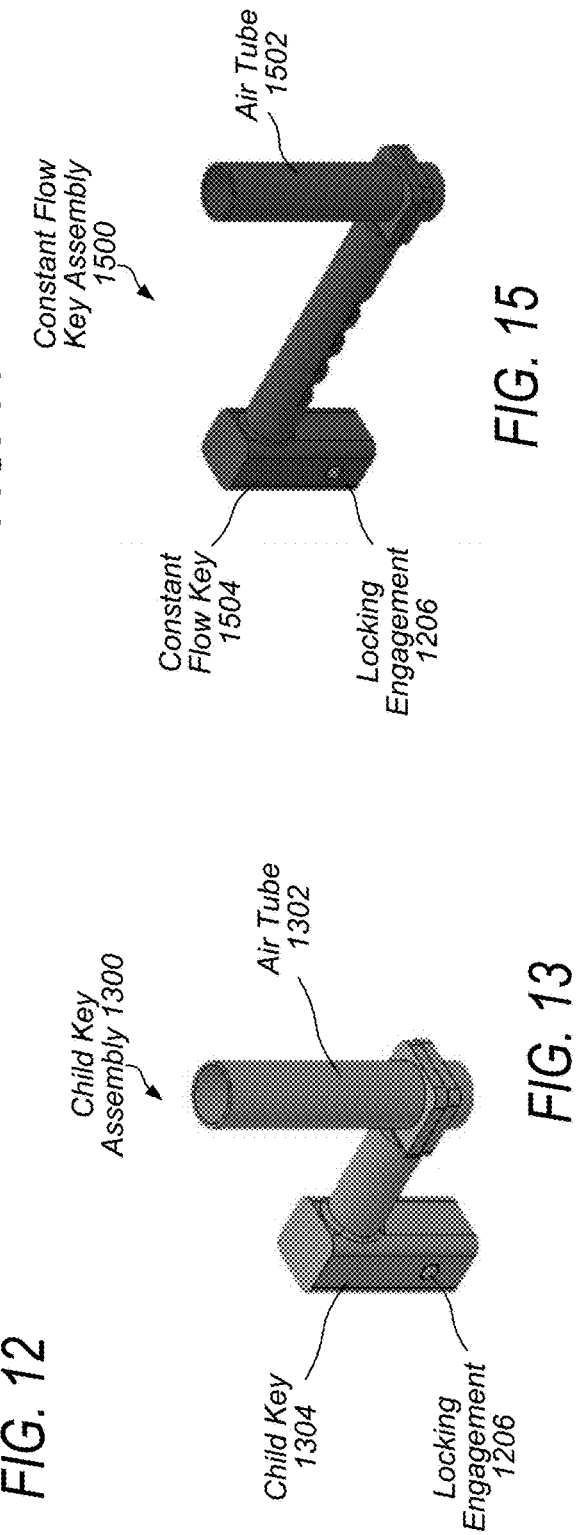

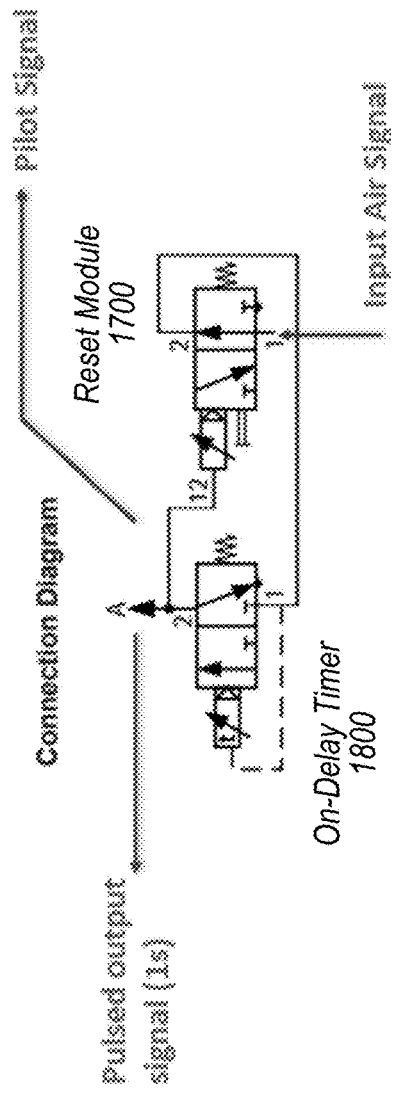
FIG. 19
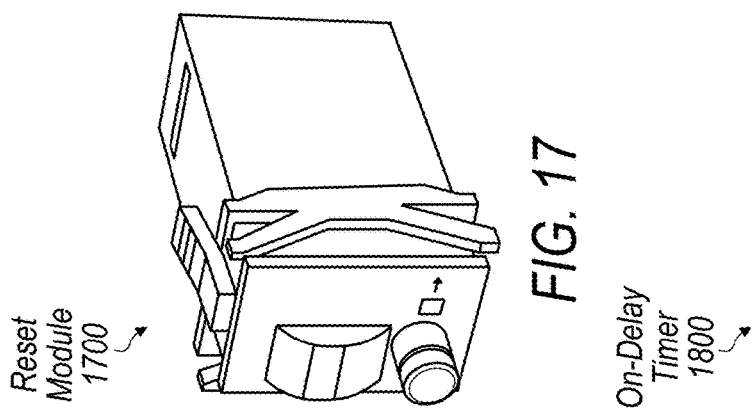
FIG. 17
FIG. 18

AUTOMATIC RESCUE BREATHING UNIT WITH KEYING SYSTEM

PRIORITY CLAIM

This application claims the benefit of priority to U.S. Provisional Application No. 63/386,435 filed Dec. 7, 2022, which is incorporated hereby by reference.

BACKGROUND

1. Field of the Invention

The disclosed embodiments generally relate to a system and method for providing air/oxygen to a subject, and more particularly to a mask keying mechanism for determining breath profile and parameters to be delivered by the air/oxygen system.

2. Description of Related Art

Medical emergencies often call on one or more people to provide life-saving support. For example, CPR may be performed when a person is not breathing, or breathing inadequately (e.g., during cardiac arrest). CPR generally involves providing air into a person's lungs via the mouth, or mouth and nose, and/or performing a series of chest compressions. This may be performed repeatedly to help oxygenate and circulate the blood. Blowing air into the victim's mouth forces air into the lungs to replace spontaneous respiration and compressing the chest compresses the heart to maintain blood circulation. In a situation in which the heart has stopped beating, performing CPR is intended to maintain a flow of oxygenated blood to the brain and heart, thereby delaying tissue death and extending the opportunity for a successful resuscitation without permanent brain damage. Defibrillation and other advanced life support techniques may also be used to improve the outcome for a victim of cardiac arrest.

CPR techniques can vary depending on the person needing assistance. For example, administering CPR to an adult generally includes providing a set number of full breaths via the mouth, whereas administering CPR to an infant or child may require a larger number of smaller breaths or puffs via the mouth and/or nose. The lower pressure and larger numbers of breaths administered to an infant or child may reduce the likelihood of injury to the respiratory system of the infant or child. Similarly, the force used in administering the chest compressions is reduced when administering CPR to an infant or child. Accordingly, a person who administers CPR must consider several variables and remember a variety of protocols.

CPR is more effective the sooner it is initiated and thus, the time between the onset of the medical emergency and the time of initiating CPR may be critical. Brain cells may begin to die in as little as 4-6 minutes without an adequate supply of oxygen. Unfortunately, medical emergencies can, and often do, happen at locations that are remote to medical facilities and where no trained medical professionals are readily available and, thus, a by-stander may be in the best position to perform CPR.

BRIEF DESCRIPTION OF THE DRAWINGS

Advantages of the present invention will become apparent to those skilled in the art with the benefit of the following detailed description of embodiments and upon reference to the accompanying drawings in which:

FIG. 6 depicts a perspective representation of an inlet adapter, according to some embodiments.

FIG. 7 depicts a perspective representation of a manifold, according to some embodiments.

FIG. 7A depicts a perspective representation of a pressure relief valve, according to some embodiments.

FIG. 8 depicts a perspective representation of an on/off valve, according to some embodiments.

FIG. 9 depicts a perspective representation of an on/off valve in a mounting assembly, according to some embodiments.

FIG. 10 depicts a perspective representation of a keyhole assembly, according to some embodiments.

FIG. 11 depicts a perspective representation of four keyhole assemblies with four keyholes, according to some embodiments.

FIG. 12 depicts a perspective representation of an adult key assembly, according to some embodiments.

FIG. 13 depicts a perspective representation of a child key assembly, according to some embodiments.

FIG. 14 depicts a perspective representation of an infant key assembly, according to some embodiments.

FIG. 15 depicts a perspective representation of a constant flow key assembly, according to some embodiments.

FIG. 17 depicts an example representation of a reset module, according to some embodiments.

FIG. 18 depicts an example representation of an on-delay timer, according to some embodiments.

FIG. 19 depicts a schematic representation of a pneumatic circuit to provide pulsed air flow with a reset module and on-delay timer, according to some embodiments.

Figure 1:
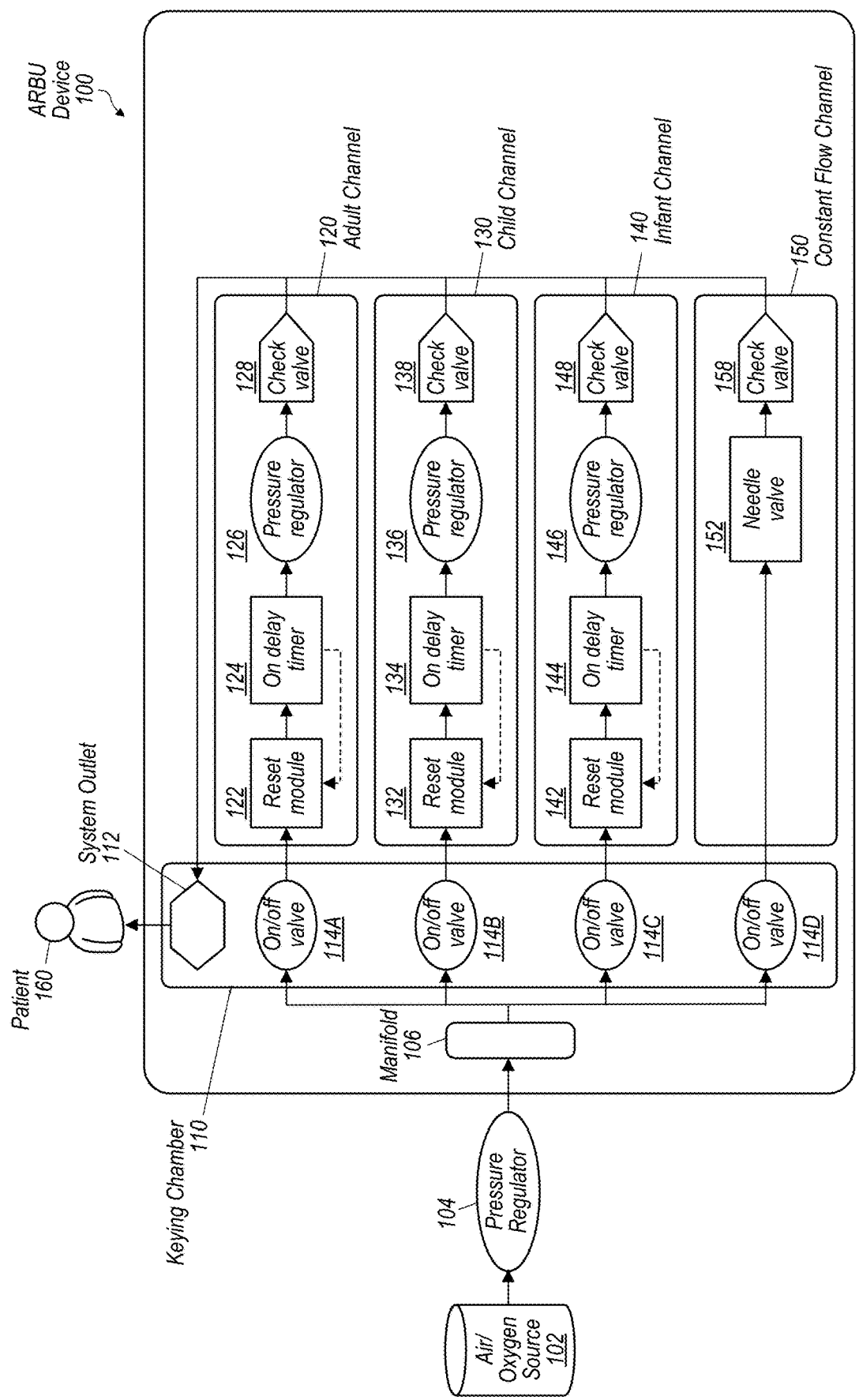
FIG. 1 depicts a block diagram overview of an ARBU (automatic rescue breathing unit) system, according to some embodiments.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF EMBODIMENTS

When cardiac arrest occurs, the heart stops beating. The loss of heart function causes oxygen content, the amount of usable oxygen in the blood, to be depleted. Cardiopulmonary resuscitation (CPR) on the cardiac arrest victim is required immediately. CPR consists of delivering chest compressions and air/oxygen (rescue breaths) to the patient. The goal of CPR is for the return of spontaneous circulation of blood to the body. Developments have been made in automatic rescue breathing units (ARBUs) in the treatment of patients suffering cardiac arrest to increase the chances of survival. Even with the implementation of ARBUs, however, errors can be made, even by trained professionals, that may decrease the chances of survival. Errors may, for instance, be made in the rates and volumes of rescue breaths provided to the patient due to the complexities involved in remembering and delivering appropriate rates and volumes for different types (e.g., ages or sizes) of patients.

The present disclosure contemplates various embodiments of an automatic rescue breathing unit (ARBU) that includes two sub-systems—an airway device keying mechanism and a ventilation unit where the keying mechanism triggers and determines breath profile and parameters delivered by the ventilation unit. FIG. 1 depicts a block diagram overview of an ARBU system, according to some embodiments. In the illustrated embodiment, the ARBU system includes ARBU device 100 connected to air/oxygen source 102 via pressure regulator 104. ARBU device 100 includes manifold 106, keying chamber 110, adult channel 120, child channel 130, infant channel 140, and constant flow channel 150.

In various embodiments, device 100 is connected to patient 160 to provide oxygen/air flow to the patient. For instance, an airway device intended to be placed on the airway of patient 160 is coupled to system outlet 112 of keying chamber 110. As described herein, an "airway device" may include any of, but not be limited to, masks, endotracheal tubes, laryngeal mask airways, Igels, King airways, or any other airway device suitable for providing a flow or pulse of air to patient 160. In certain embodiments, system outlet 112 is the only air outlet on device 100. Having only a single outlet from device 100 may prevent undesired use of the device, as described herein. When device 100 is activated, compressed oxygen/air from air/oxygen source 102 (e.g., an oxygen tank) flows into manifold 106 through pressure regulator 104. Pressure regulator 104 controls a pressure of oxygen drawn into manifold 106. For example, pressure regulator 104 may limit the pressure to prevent overpressure in device 100. In one embodiment, pressure is regulated to a pressure of 50 psi through pressure regulator 104.

In certain embodiments, manifold 106 has five outlets (see, e.g., FIG. 7), four of which connect into keying chamber 110, with each outlet connected to one of the four channels (e.g., adult channel 120, child channel 130, infant channel 140, and constant flow channel 150) in device 100 by independently operated on/off valves 114A-D in keying chamber 110. The fifth outlet of manifold 106 may connect to a pressure relief valve (e.g., pressure relief valve 109, shown in FIG. 7A and described below). In various embodiments, on/off valve 114A corresponds to adult channel 120, on/off valve 114B corresponds to child channel 130, on/off valve 114C corresponds to infant channel 140, and on/off valve 114D corresponds to constant flow channel 150. Accordingly, activation of each channel is independently controlled by its corresponding on/off valve 114A-D in keying chamber 110. Depending on the size of the airway device coupled to system outlet 112, keying chamber 110 (e.g., the keying mechanism) may activate one of the four channels (e.g., one of adult channel 120, child channel 130, infant channel 140, or constant flow channel 150) to deliver the required breath profile to patient 160. For example, keying chamber 110 may open the on/off valve 114 for the channel to be activated and the remaining on/off valves will remain closed. Accordingly, the activated channel receives air flow from manifold 106 while air flow is inhibited to the other channels according to the airway device detected by the keying mechanism.

In various embodiments, device 100 has size dimensions that are at most 35 cm×25 cm×15 cm. Device 100 may also have a weight of at most 15 pounds (e.g., about 6.8 kg). Having smaller dimensions and/or weight may enable device 100 to be portable and more easily maneuverable by personnel. In certain embodiments, device 100 does not include any electric components. Not having electric components in device 100 may eliminate electrical shock hazard when using the device. Further, device 100 may not have any knobs or other adjustment controls on the device that allow user adjustment of the device. Removing user adjustments may, in such embodiments, inhibit undesirable changes to the operating parameters of device 100.

As described above, the flow/respiratory parameters for device 100 may be determined based on the airway device size coupled to the device. The flow/respiratory parameters may be determined by rescue breath parameters defined by the American Heart Association. Table I provides example flow/respiratory parameters to be provided by device 100 according to airway device size.

TABLE I

| Airway Device Size | Flow Rate (L/min)* | Tidal Volume (cc) | Peak Pressure (cm of H$_2$O) | Respiration Rate (bpm)** |
|---|---|---|---|---|
| Adult | 30 ± 10 | 600 ± 10% | 40 ± 10% | 10 |
| Child | 15 ± 5 | 300 ± 10% | 20 ± 10% | 20 |
| Infant | 5 ± 2 | 100 ± 10% | 20 ± 10% | 30 |
| Constant Flow | 15 | — | — | — |

*Flow rate is a function of tidal volume and rate
**There is intended to be no fluctuations in respiration rate In TABLE I, the peak pressure refers to the maximum air pressure in the chest cavity to which the patient will be exposed. Tidal volume refers to the volume of air/oxygen that will be provided to the patient during each inhalation and the respiratory rate refers to the number of breaths that will be provided to the patient by device 100 over a period of time (e.g., over a minute).

For the illustrated embodiment of FIG. 1, adult channel 120 is configured to provide flow/respiratory parameters corresponding to the adult airway device size in TABLE I, child channel 130 is configured to provide flow/respiratory parameters corresponding to the child airway device size in TABLE I, infant channel 140 is configured to provide flow/respiratory parameters corresponding to the infant airway device size in TABLE I, and constant flow channel 150 is configured to provide flow/respiratory parameters corresponding to the constant flow airway device size in TABLE I. As shown in FIG. 1, each of adult channel 120, child channel 130, and infant channel 140 includes a pneumatic timing circuit with a reset module (122, 132, and 142 in the channels, respectively) and an on-delay pneumatic timer (124, 134, 144 in the channels, respectively). In the channels, pulsed oxygen outputs from the pneumatic timing circuit (220, 230, and 240 in the channels, respectively, shown in FIG. 3) are passed into a pressure regulator (126, 136, and 146 in the channels, respectively). The pressure regulators control the input pressure to regulate the input pressure and convert it to the flow rate needed for the specific channel. For instance, an input flow rate pressure of 50 psi may be reduced to a flow rate of 6 L/min in adult channel 120 by pressure regulator 126. After the downregulation, the air/oxygen is passed through a check valve (128, 138, and 148 in the channels, respectively) and then to system outlet 112.

In certain embodiments, constant flow channel 150 includes needle valve 152 and check valve 158. Needle valve 152 is used to control the flow rate through constant flow channel 150 without any pressure regulation. In various embodiments, components in the channels are coupled using pneumatic tubing (e.g., 6 mm pneumatic tubing) with NPT push-to-connect adapters for fittings to the components. Teflon tape or another sealing material may also be used on the adapters to inhibit air leakage in device 100.

Figure 2:
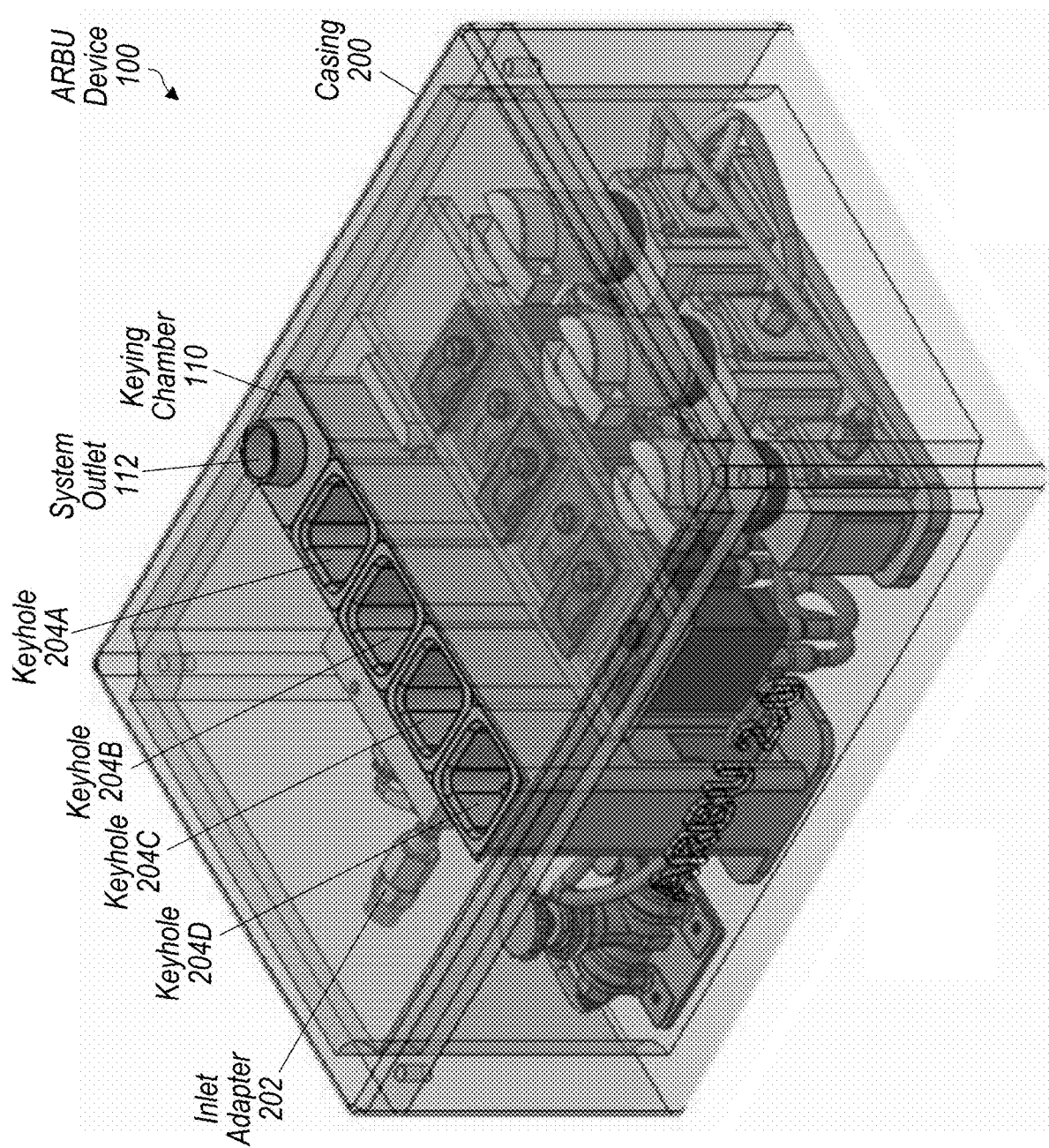
FIG. 2 depicts an isometric view representation of an ARBU device, according to some embodiments.
Figure 3:
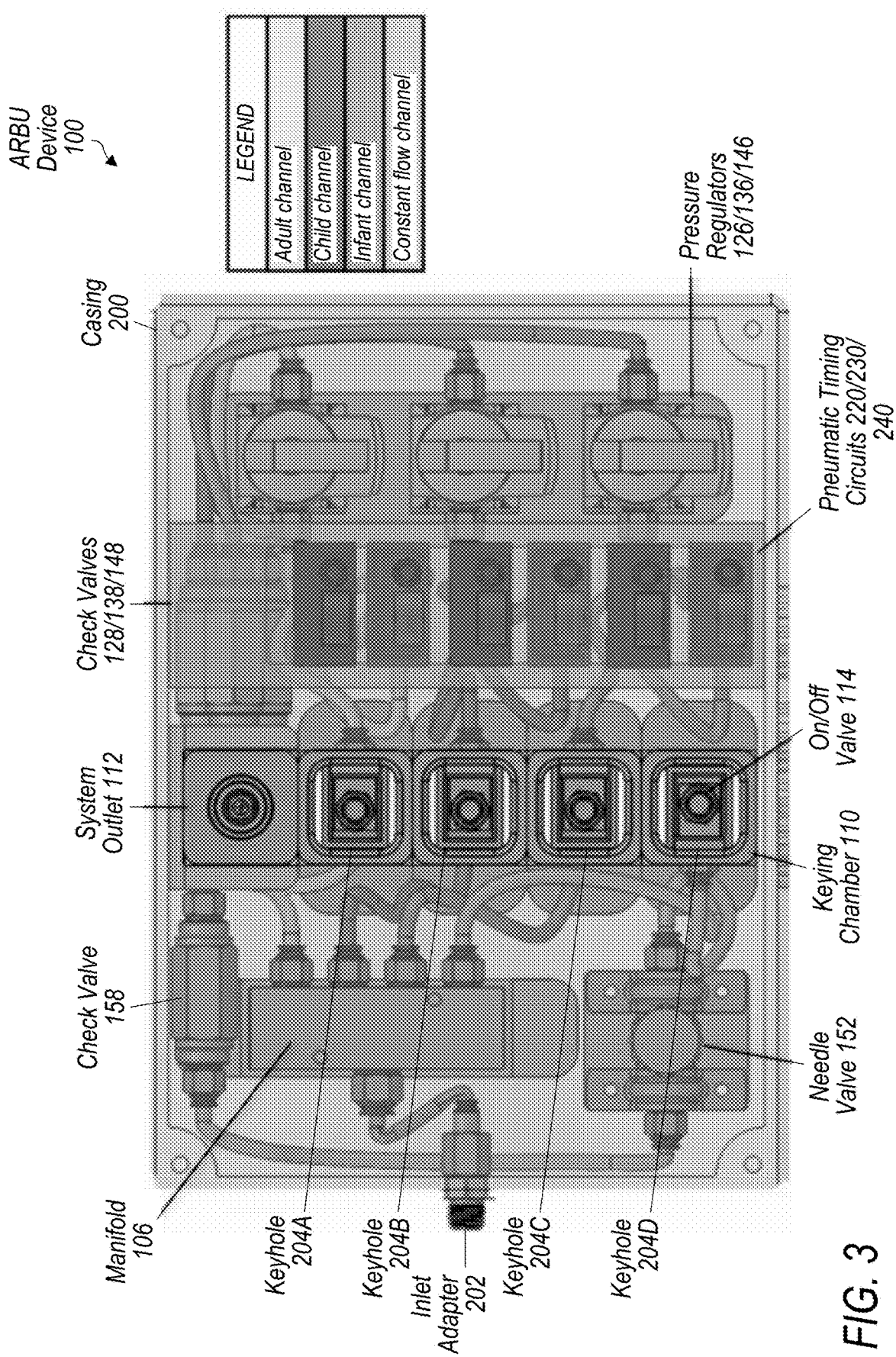
FIG. 3 depicts a top view representation of an ARBU device, according to some embodiments.
Figure 4:
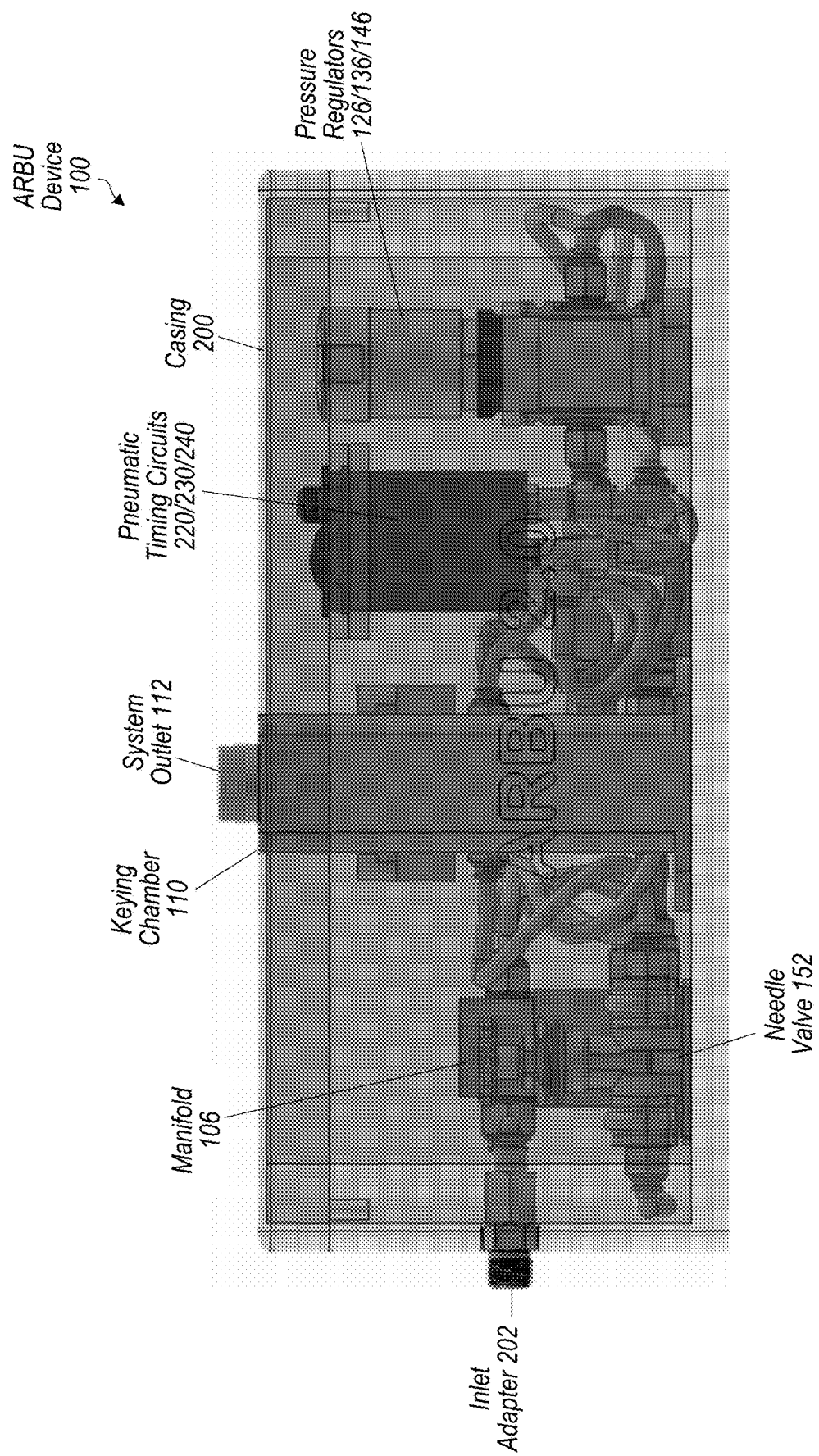
FIG. 4 depicts a front view representation of an ARBU device, according to some embodiments.
Figure 5:
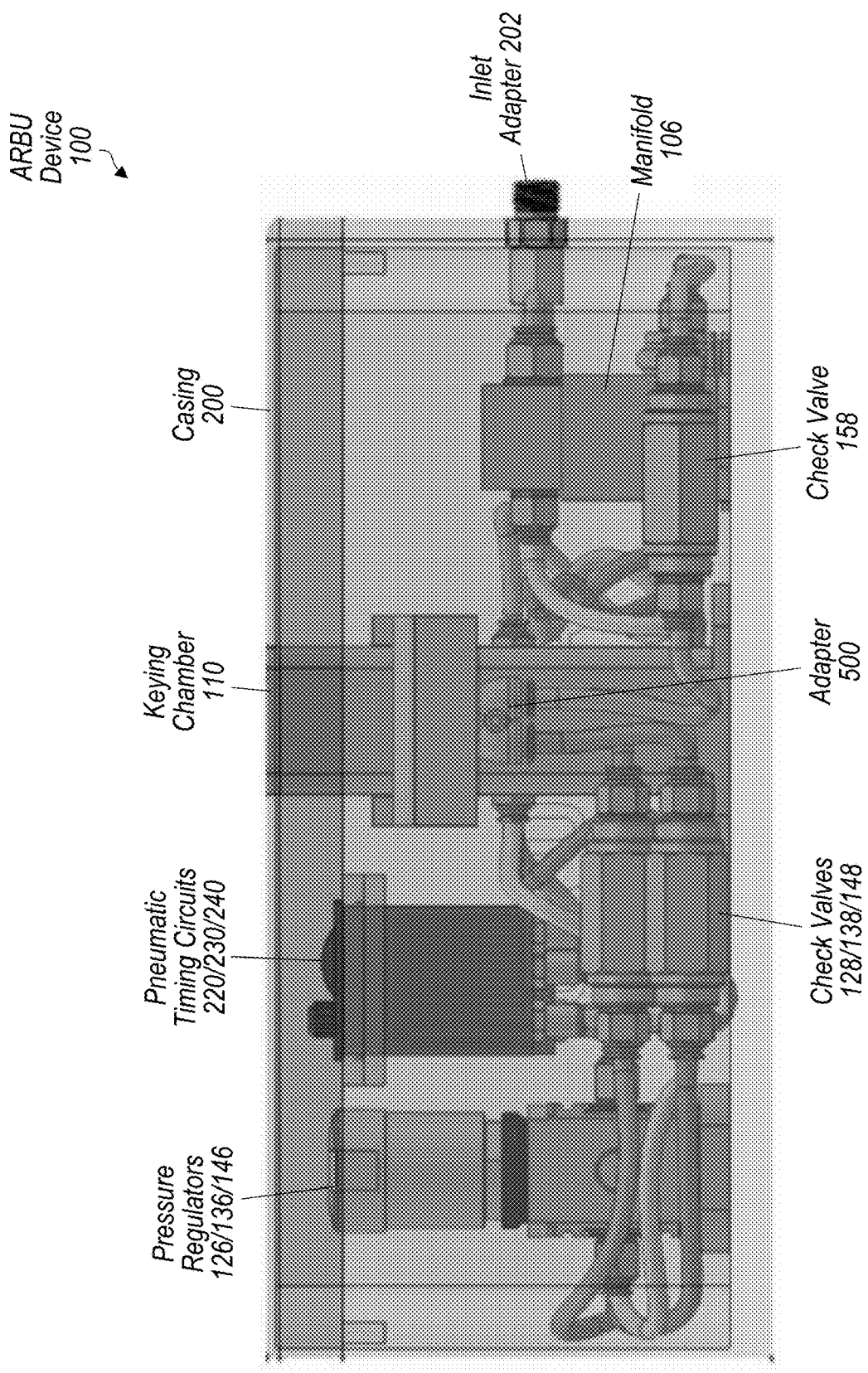
FIG. 5 depicts a back view representation of an ARBU device, according to some embodiments.

FIG. 2 depicts an isometric view representation of device 100, according to some embodiments. FIG. 3 depicts a top view representation of device 100, according to some embodiments. FIG. 4 depicts a front view representation of device 100, according to some embodiments. FIG. 5 depicts a back view representation of device 100, according to some embodiments. In the illustrated embodiments, the components of device 100 are located inside casing 200 (which is transparent in the drawings). Inlet adapter 202 is connected to manifold 106 to provide an air/oxygen inlet to device 100. For example, inlet adapter 202 may connect manifold 106 to pressure regulator 104, shown in FIG. 1.

FIG. 6 depicts a perspective representation of inlet adapter 202, according to some embodiments. In various embodiments, inlet adapter 202 is designed to protrude out of casing 200 of device 100, as shown in FIG. 3. In certain embodiments, inlet adapter 202 is a hose fitting designed for compressed gas. For example, in one embodiment, inlet adapter 202 is a 6 mm outside diameter×¼ NPT push-to-connect adapter.

FIG. 7 depicts a perspective representation of manifold 106, according to some embodiments. Air/oxygen may enter manifold 106 through inlet adapter 202 and pressurize the manifold. In certain embodiments, manifold 106 includes one inlet (e.g., inlet 107 connected to inlet adapter 202) and five outlets 108. In one embodiment, four outlets 108 are connected to on/off valves 114A-D and one outlet 108 is connected to pressure relief valve 109. FIG. 7A depicts a perspective representation of pressure relief valve 109, according to some embodiments, that may be connected to one outlet 108 of manifold 106. Pressure relief valve 109 may be coupled to manifold 106 to inhibit excessive pressure in device 100. In some embodiments, the inlet of manifold 106 is a female port with ⅜ NPT threading and the outlets are female ports with ¼ NPT threading. The inlet/ outlets of manifold 106 may be connected to push-to-connect fittings. In certain embodiments, the inlet is on one side of manifold 106 and the outlets are on the opposite side of the manifold. Having the inlet/outlets on opposite sides allows air/oxygen to flow in a straight path and improve air flow through device 100. In one embodiment, manifold 106 is aluminum (e.g., anodized aluminum).

In various embodiments, the outlets of manifold 106 are connected to on/off valves 114A-D in keying chamber 110, in addition to pressure relief valve 109. FIG. 8 depicts a perspective representation of on/off valve 114, according to some embodiments. In certain embodiments, on/off valve 114 is a push button valve where the valve is normally off (e.g., off when the button is not pushed). Thus, when an airway device key (described below) pushes on the button, on/off valve 114 is opened to allow air to flow through the valve. For instance, on/off valve 114 may include a spring that normally closes off the valve until the button is pushed down (e.g., depressed or activated). Accordingly, when the button is pushed down (e.g., activated) to overcome the force of the spring, air flows through the valve. When the button is released and moves upwards, the spring closes the valve and closes off air flow through the valve. On/off valve 114 may include an exhaust port through which air is released when closed to inhibit over pressurization of the valve.

In various embodiments, on/off valve 114 is placed in a mounting assembly for placement in keying chamber 110. FIG. 9 depicts a perspective representation of on/off valve 114 in mounting assembly 900, according to some embodiments. Mounting assembly 900 may be, for example, a 3D printed mounting assembly. In some embodiments, mounting assembly 900 is configured to be mounted to a base of casing 200 or another rigid structure. Mounting of mounting assembly 900 may ensure stability of on/off valve 114 during operation of the valve (e.g., during pushing of the valve to open the valve).

In certain embodiments, mounting assembly 900, with on/off valve 114, is placed inside a keyhole assembly for positioning in keying chamber 110. FIG. 10 depicts a perspective representation of keyhole assembly 1000, according to some embodiments. In the illustrated embodiment, mounting assembly 900 is positioned (with on/off valve 114) in a lower portion of keyhole assembly 1000. Keyhole assembly 1000 may be, for example, a 3D printed assembly. Keyhole assembly 1000 includes keyhole 204 that allows access to the push button of on/off valve 114. Keyhole 204 may, for instance, allow a key (described below) to be inserted and activate (e.g., depress) the push button of on/off valve 114.

FIG. 11 depicts a perspective representation of four keyhole assemblies 1000A-D with four keyholes 204A-D, according to some embodiments. The four keyholes 204A-D, shown in FIG. 11, correspond to the four keyholes 204A-D, shown in FIGS. 2 and 3. Each of the keyholes 204A-D provides access to an on/off valve 114A-D that corresponds to one of the channels (e.g., one of adult channel 120, child channel 130, infant channel 140, or constant flow channel 150). For instance, keyhole 204A and on/off valve 114A may correspond to adult channel 120, keyhole 204B and on/off valve 114B may correspond to child channel 130, keyhole 204C and on/off valve 114C may correspond to infant channel 140, and keyhole 204D and on/off valve 114D may correspond to constant flow channel 150.

With keyholes 204A-D arranged as shown in FIGS. 2 and 3, various embodiments may be contemplated where key assemblies (which may be 3D printed) are designed to connect to system outlet 112 and activate an on/off valve 114 within keyhole 204 that corresponds to the key assembly 1000. Thus, a specific key assembly 1000 may be designed to be attached to an airway device with a specific intended use (e.g., use for an adult, a child, an infant, or constant flow) and the specific key assembly may engage only with the keyhole 204 and on/off valve 114 associated with the airway device's intended use. For example, an adult key assembly attached to an adult airway device may only engage keyhole 204A, which is associated with adult channel 120, such that only the on/off valve 114A for the adult channel is activated when using the adult key assembly.

FIG. 12 depicts a perspective representation of adult key assembly 1200, according to some embodiments. In the illustrated embodiment, adult key assembly 1200 includes air tube 1202 and adult key 1204. Air tube 1202 is configured to be attached to system outlet 112 in keying chamber 110. When air tube 1202 is attached to system outlet 112, key 1204 is configured to engage the on/off valve 114A through keyhole 204A. For instance, the distance between air tube 1202 and key 1204 is defined such that when air tube 1202 is connected to system outlet 112, the key fits into keyhole 204A and engages on/off valve 114A. In certain embodiments, when air tube 1202 is fully connected to system outlet 112, key 1204 depresses the push button of on/off valve 114A and opens the valve to allow air flow through adult channel 120. When adult key assembly 1200 is removed, on/off valve 114A closes again and cuts off air flow through adult channel 120. In some embodiments, adult key assembly 1200 includes locking engagement 1206, which is discussed in more detail below.

FIG. 13 depicts a perspective representation of child key assembly 1300, according to some embodiments. In the illustrated embodiment, child key assembly 1300 includes air tube 1302 and child key 1304. The distance between air tube 1302 and child key 1304 is defined such that when air tube 1302 is connected to system outlet 112, the child key fits into keyhole 204B and engages on/off valve 114B. Thus, when air tube 1302 is fully connected to system outlet 112, child key 1304 depresses the push button of on/off valve 114B and opens the valve to allow air flow through child channel 130. When child key assembly 1300 is removed, on/off valve 114B closes again and cuts off air flow through child channel 130. In some embodiments, child key assembly 1300 includes locking engagement 1206, which is discussed in more detail below.

FIG. 14 depicts a perspective representation of infant key assembly 1400, according to some embodiments. In the illustrated embodiment, infant key assembly 1400 includes air tube 1402 and infant key 1404. The distance between air tube 1402 and infant key 1404 is defined such that when air tube 1402 is connected to system outlet 112, the infant key fits into keyhole 204C and engages on/off valve 114C. Thus, when air tube 1402 is fully connected to system outlet 112, infant key 1404 depresses the push button of on/off valve 114C and opens the valve to allow air flow through infant channel 140. When infant key assembly 1400 is removed, on/off valve 114C closes again and cuts off air flow through infant channel 140. In some embodiments, infant key assembly 1400 includes locking engagement 1206, which is discussed in more detail below.

FIG. 15 depicts a perspective representation of constant flow key assembly 1500, according to some embodiments. In the illustrated embodiment, constant flow key assembly 1500 includes air tube 1502 and constant flow key 1504. The distance between air tube 1502 and constant flow key 1504 is defined such that when air tube 1502 is connected to system outlet 112, the constant flow key fits into keyhole 204D and engages on/off valve 114D. Thus, when air tube 1502 is fully connected to system outlet 112, constant flow key 1504 depresses the push button of on/off valve 114D and opens the valve to allow air flow through constant flow channel 150. When constant flow key assembly 1500 is removed, on/off valve 114D closes again and cuts off air flow through constant flow channel 150. In some embodiments, constant flow key assembly 1500 includes locking engagement 1206, which is discussed in more detail below.

As shown by the various embodiments of key assemblies depicted in FIGS. 12-15, the keys can have defined distances from the air tube that connects to system outlet 112 such that, when a particular key assembly is utilized, only a specific channel associated with the key assembly is opened to air flow. Thus, with the specific key assemblies being designated for specific types of airway devices (e.g., adult key assembly 1200 for an adult airway device, child key assembly 1300 for a child airway device, infant key assembly 1400 for an infant airway device, and constant flow key assembly 1500 for a constant flow airway device), selection of the proper channel flow for air through device 100 automatically occurs. In other words, when a user selects an airway device (e.g., an adult airway device) with the appropriate key assembly already attached to the airway device (e.g., adult key assembly 1200), the proper air channel (e.g., adult channel 120) is automatically selected when the user attaches the key assembly to system outlet 112 on device 100. In various embodiments, key assemblies 1200, 1300, 1400, 1500 include ergonomic features or textured features to ease handling of the key assemblies. These features may also provide indication to personnel of the differences between the key assemblies.

Automatic selection of the proper air channel as described herein provides a safe and secure method for selection of the proper air channel and its associated flow/respiratory parameters (as shown in TABLE I) based on selection of an airway device. Giving CPR and providing assisted air is often done in a high stress situation where humans can easily make mistakes. Device 100, with its automatic selection of air channel and flow/respiratory parameters, mitigates many risks associated with human decision-making and makes for a safer and more reliable administration of life-saving techniques.

Figure 16A:
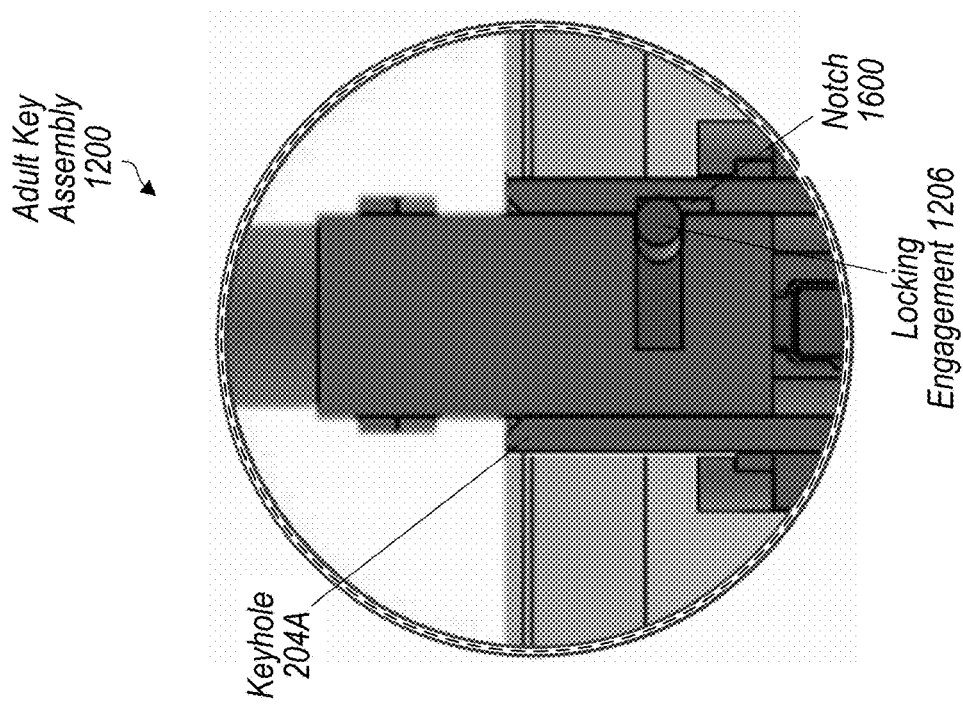
FIG. 16A depicts an enlarged view of a locking engagement engaged with a notch of a keyhole.
Figure 16:
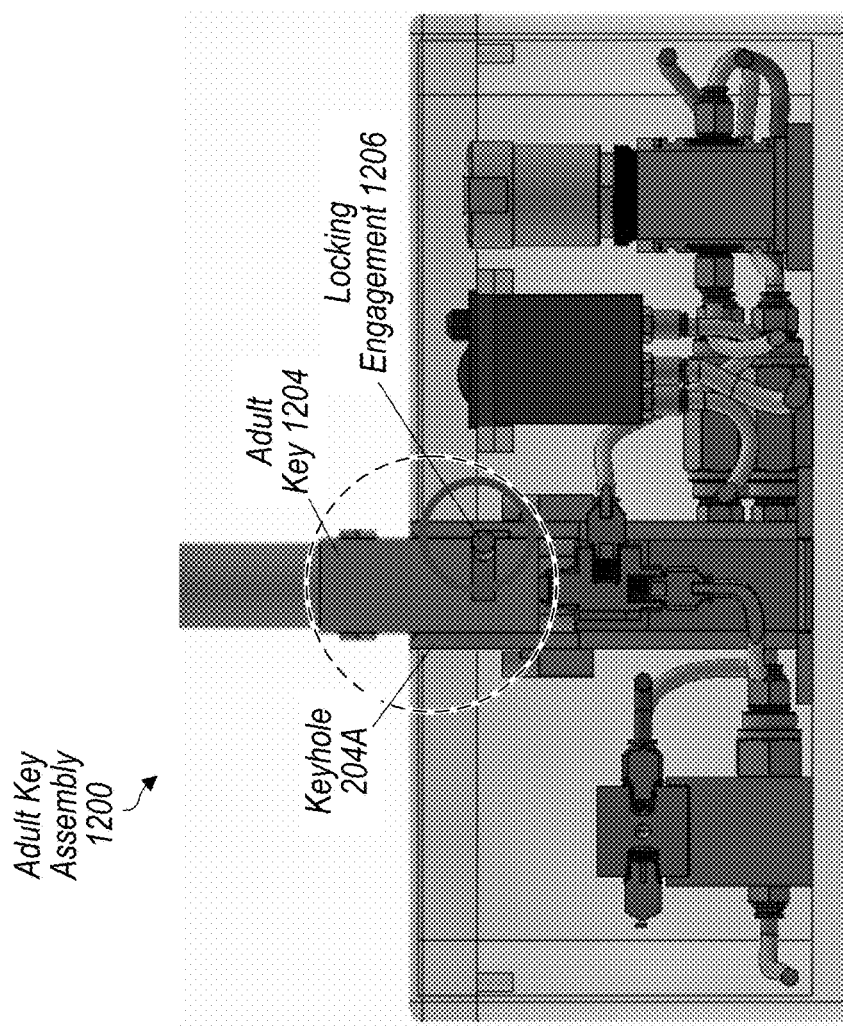
FIG. 16 depicts a side-view representation of an adult key on an adult key assembly inserted in a keyhole, according to some embodiments.

In some embodiments, as shown in FIGS. 12-15, a key assembly includes locking engagement 1206. Locking engagement 1206 may be, for example, a spring-ball detent press-fit into the key or another engagement component that is part of a locking mechanism to secure the key assembly in a keyhole. FIG. 16 depicts a side-view representation of adult key 1204 on adult key assembly 1200 inserted in keyhole 204A, according to some embodiments. FIG. 16A depicts an enlarged view of locking engagement 1206 engaged with notch 1600 of keyhole 204A. Locking engagement 1206 and notch 1600 may together form the locking mechanism for the key assembly.

In some embodiments, as adult key 1204 is inserted into keyhole 204A, locking engagement 1206 (e.g., the ball) is pushed inwards on the key and then pops back out when the locking engagement 1206 engages notch 1600. As shown in FIGS. 16 and 16A, when key assembly 1200 and key 1204 is fully inserted in keyhole 204A, locking engagement 1206 engages notch 1600 and the key is secured in the keyhole. The engagement between locking engagement 1206 and notch 1600 may be overcome by a small force imparted by the user when the user wants to disengage key assembly 1200 from device 100. The locking mechanism provided by locking engagement 1206 and notch 1600 may inhibit accidental displacement of the key assembly and its air tube during use of device 100. In various embodiments, key assemblies are made of materials suitable for repeated insertion and removal of the key assemblies. For instance, the key assemblies may be made of carbon fiber infused nylon or other high strength, low weight materials.

As described above, adult channel 120, child channel 130, and infant channel 140 have pneumatic timing circuits (shown in FIG. 3) associated with the channels. For instance, adult channel 120 is associated with pneumatic timing circuit 220, child channel 130 is associated with pneumatic timing circuit 230, and infant channel 140 is associated with pneumatic timing circuit 240. Pneumatic timing circuits 220, 230, 240 are implemented to control the breathing parameters (e.g., breaths per minute and/or breath volume) provided by each of the channels 120, 130, 140, respectively. A pneumatic timing circuit may include a reset module and an on-delay timer.

Accordingly, in certain embodiments, pneumatic timing circuit 220 includes reset module 122 and on-delay timer 124 in adult channel 120, pneumatic timing circuit 230 includes reset module 132 and on-delay timer 134 in child channel 130, and pneumatic timing circuit 240 includes reset module 142 and on-delay timer 144 in infant channel 140. Pneumatic timing circuits 220, 230, 240 may operate to provide the flow/respiratory parameters listed in TABLE I for each of channels 120, 130, 140, respectively. The reset modules and on-delay timers work in combination to provide pulsed air flow through the channels with the proper parameters.

FIG. 17 depicts an example representation of a reset module 1700, according to some embodiments. FIG. 18 depicts an example representation of an on-delay timer 1800, according to some embodiments. Both reset module 1700 and on-delay timer 1800 may be components made by Impulse Automation Ltd (Andover, United Kingdom). FIG. 19 depicts a schematic representation of a pneumatic circuit to provide pulsed air flow with a reset module and on-delay timer, according to some embodiments. In various embodiments, reset module 1700 is used to reset on-delay timer 1800 to create a continuous timing circuit.

In the illustrated embodiment of the pneumatic circuit, input air is connected to port 1 of reset module 1700 and, in response, on-delay timer 1800 begins to count the time (on-delay timer 1800 receiving air from port 2 of reset module 1700 through port 1 on the on-delay timer). Air is then passed from port 1 to port 2 of on-delay timer 1800, which is connected to port 12 of reset module 1700 as a pilot signal through a tube splitter on timeout. As one example, for a pulsed output of 1 second, after an output of 1 second (A), the air supply from port 2 of reset module 1700 to port 1 of on-delay timer 1800 is interrupted for 300 milliseconds, which resets on-delay timer 1800 and reset module 1700. This cycle will run continuously for as long as air is connected (e.g., supplied) to port 1 of reset module 1700. It should be noted that the timing may vary for different breath profiles (e.g., different timing may be implemented for an adult breath profile and a child breath profile).

Figure 20:
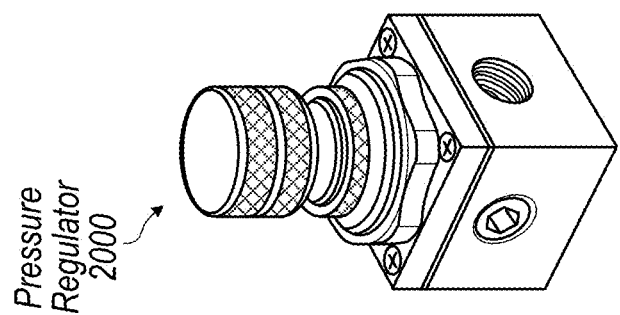
FIG. 20 depicts an example representation of a pressure regulator, according to some embodiments.

After the pneumatic timing circuits, air in channels 120, 130, 140 flows through a pressure regulator (e.g., pressure regulator 126, 136, 146, respectively, in the channels). The pressure regulator brings down the pressure to the desired value for its associated channel. FIG. 20 depicts an example representation of a pressure regulator 2000, according to some embodiments. Pressure regulator 2000 may be, for example, a pressure regulator manufactured by Ellis/Kuhnke Controls (Eatontown, New Jersey).

Figure 21:
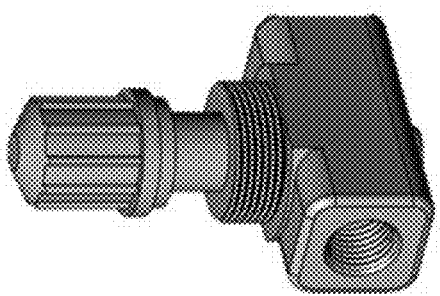
FIG. 21 depicts an example representation of a needle valve, according to some embodiments.

In various embodiments, constant flow channel 150 includes needle valve 152, as shown in FIG. 1. FIG. 21 depicts an example representation of a needle valve 152, according to some embodiments. Needle valve 152 may be, for example, a needle valve obtained from McMaster-Carr Supply Company (Elmhurst, Illinois). Needle valve 152 may be chosen for providing the constant flow of air as a needle valve is a pneumatic device that can provide a constant flow rate. For instance, needle valve 152 may include a tapered pin that gradually opens a chamber to provide a fine flow of air. In certain embodiments, needle valve 152 includes a knob that is set to tune the flow rate of air passing through the valve. Accordingly, needle valve 152 may be set to provide a constant flow rate of oxygen at the input pressure. In certain embodiments, needle valve 152 provides a constant flow rate of 15 L/min at an input pressure of 50 psi. In various embodiments, the knob on needle valve 152 may be locked in position after assembly of device 100 to inhibit changing of the flow rate of air passing through the valve from a determined setting.

Figure 22:
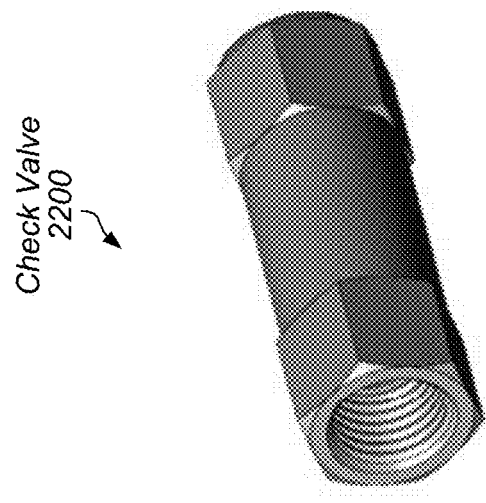
FIG. 22 depicts an example representation of a check valve, according to some embodiments.

In certain embodiments, all the channels include check valves though embodiments may be contemplated with some channels not having check valves. For instance, adult channel 120 includes check valve 128, child channel 130 includes check valve 138, infant channel 140 includes check valve 148, and constant flow channel 150 includes check valve 158, as shown in FIG. 1. FIG. 22 depicts an example representation of a check valve 2200, according to some embodiments. Check valve 2200 may be, for example, a check valve obtained from McMaster-Carr Supply Company (Elmhurst, Illinois). Check valves are unidirectional valves that may be placed at the ends of channels to ensure air/oxygen only flows in the intended direction. Accordingly, check valves may be utilized to ensure that no backflow of oxygen into device 100 occurs. In one embodiment, the check valves are brass and have a minimum opening pressure of 0.3 psi.

Figure 23:
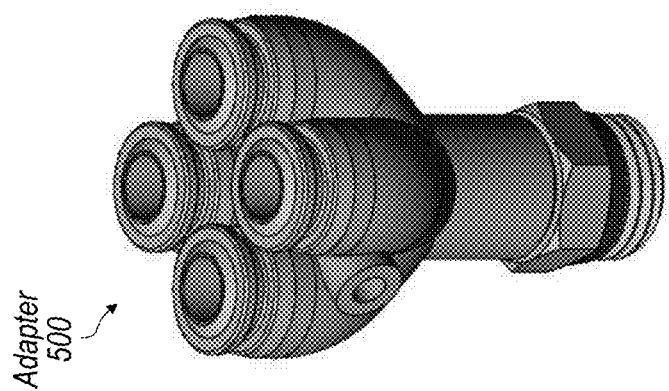
FIG. 23 depicts an example representation of an adapter, according to some embodiments.

As shown in FIG. 5, after check valves 128, 138, 148, and 158, multiple air lines enter keying chamber 110. These multiple air lines are connected to system outlet 112, which is a single outlet. In certain embodiments, adapter 500 is used to combine the multiple air lines into a single air line connected to system outlet 112. FIG. 23 depicts an example representation of adapter 500, according to some embodiments. Adapter 500 may be made of nylon or another air impermeable material. In certain embodiments, adapter 500 is a double-wye adapter with 4 inlets connected to 1 outlet to combine the flow from the 4 inlets into a single outlet flow. The inlets may be connectable to pneumatic tubing coming from check valves while the outlet may include universal threading for connecting to NPT and NPTF threads. The use of the double-wye configuration for adapter 500 allows straight line flow of pulsed oxygen signals, which requires no pressurization as would be the case for the utilization of a manifold. Adapter 500 may also utilize various gaskets and/or O-rings to inhibit air leakage from the connections to the adapter.

Figure 25:
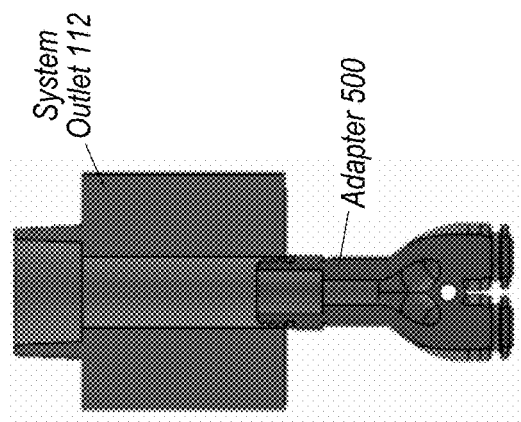
FIG. 25 depicts a cross-sectional representation of a system outlet connected to an adapter, according to some embodiments.
Figure 24:
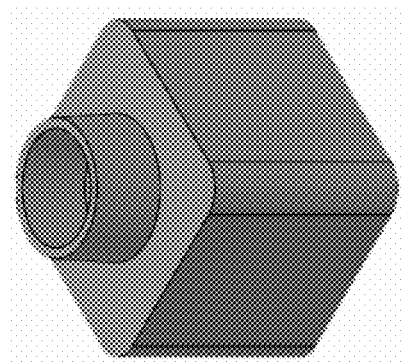
FIG. 24 depicts an example representation of a system outlet, according to some embodiments.

FIG. 24 depicts an example representation of system outlet 112, according to some embodiments. System outlet 112 may be, for example, a 3D printed nylon outlet. In some embodiments, system outlet is made of solid filled carbon infused nylon. System outlet 112 has a female connector on its lower end configured to connect to the male outlet of adapter 500. FIG. 25 depicts a cross-sectional representation of system outlet 112 connected to adapter 500, according to some embodiments. The various tubes and fittings utilized in device 100 include tubes and fittings suitable for pneumatic operation and/or a flow of air/oxygen. For instance, many tubes and fittings may be made of polyurethane rubber or other impermeable materials to inhibit leakage of oxygen from device 100.

Figure 26:
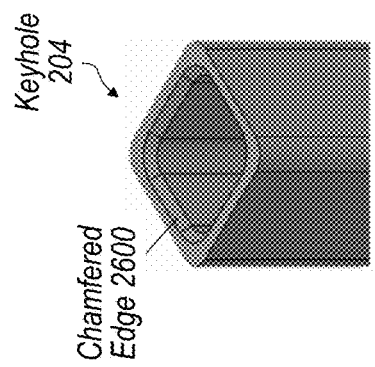
FIG. 26 depicts an example representation of a keyhole with chamfered edges, according to some embodiments.

In some contemplated embodiments, the edges of a keyhole (e.g., keyhole 204) are chamfered. FIG. 26 depicts an example representation of keyhole 204 with chamfered edges 2600, according to some embodiments. Chamfered edges 2600 may inhibit damage (e.g., chipping) to the edges of keyhole 204 during repeated use of device 100 (e.g., during repeated insertion and removal of a key).

As described herein, device 100 is a completely pneumatic device without any electrical components. Accordingly, device 100 may not be susceptible to water damage or damage from other harsh environments that can damage electrical equipment. Additionally, casing 200 may be chemically sealed to inhibit contamination of the interior of device 100 and its components.

Figure 27:
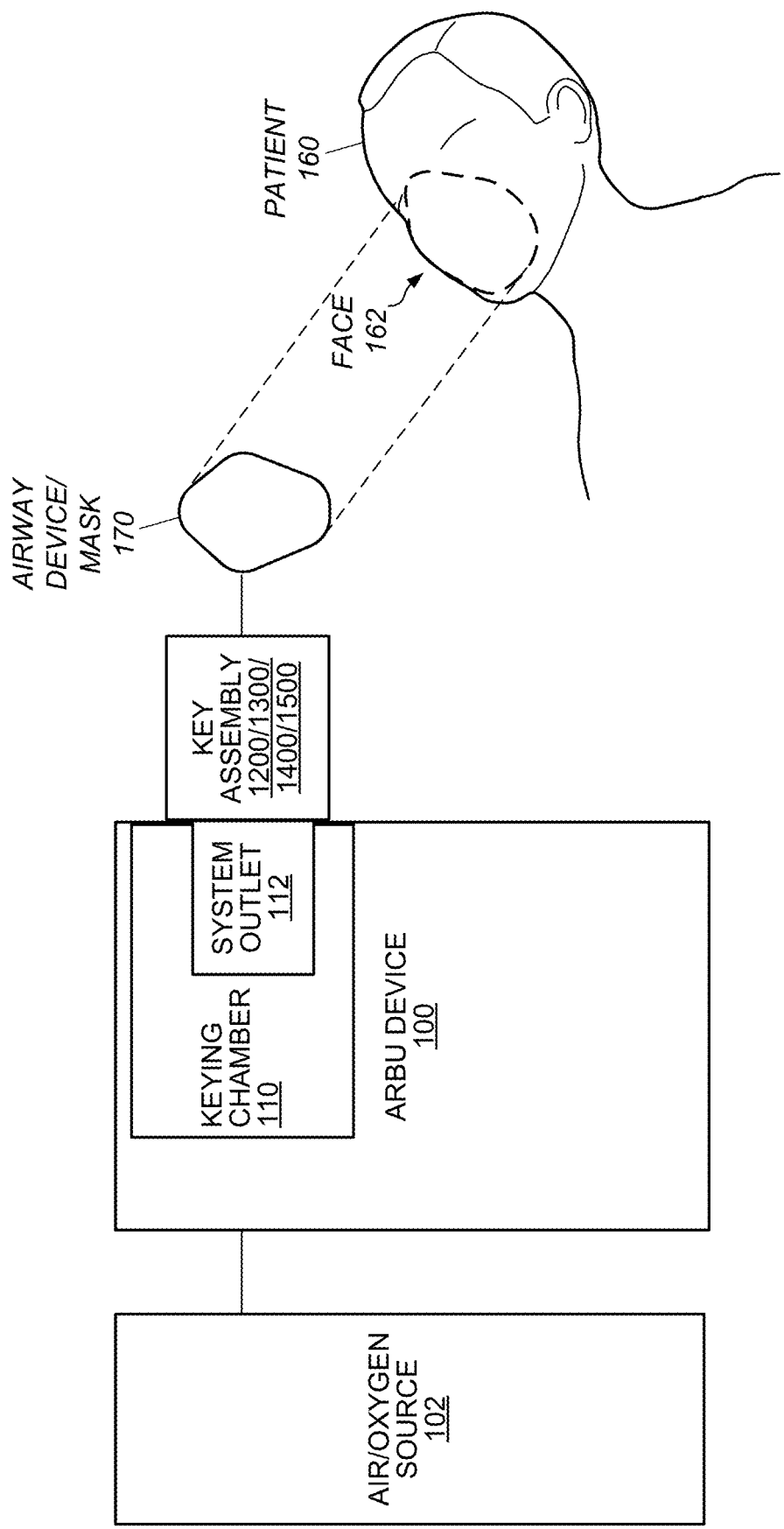
FIG. 27 depicts an example representation of implementation of an ARBU device in treatment of a patient, according to some embodiments.

FIG. 27 depicts an example representation of implementation of ARBU device in treatment of patient 160, according to some embodiments. In the illustrated embodiment, device 100 is coupled to air/oxygen source 102. Device 100 is being implemented in the treatment of patient 160, shown with face 162. In various embodiments, device 100 is a portable system that is transported to a location of patient 160.

In various embodiments, source 102 is a source capable of providing pressurized air/oxygen for use by device 100. As used herein "pressurized air/oxygen" refers to air/oxygen having a pressure that promotes the flow of the air/oxygen from device 100 into the lungs of patient 160. In some embodiments, pressurized air/oxygen may have a pressure that is above a minimum-pressure threshold, such as 20 centimeters of water (cmH$_2$O) above ambient air pressure.

In certain embodiments, source 102 is a cylinder containing pressurized air/oxygen. The pressure of the air/oxygen may be set significantly above the minimum-pressure threshold such that the air/oxygen in the cylinder is maintained above the minimum-pressure threshold as the air/oxygen is expelled from the cylinder and the pressure of the air/oxygen in the source 102 drops as a function of the air/oxygen expelled from the cylinder. Source 102 may include a mechanical device, such as a compressor, configured to move and/or pressurize the air/oxygen. Such a mechanical device may be used to pressurize and/or fill a cylinder of the source 102. In one embodiment, source 102 may include the mechanical device to move the air from the cylinder to the subject.

During treatment (e.g., resuscitation) of patient 160, airway device 170 (e.g., a mask) is coupled to face 162, or applied to the airway, of the patient. As shown in FIG. 27, key assembly (e.g., one of key assemblies 1200, 1300, 1400, or 1500) is attached to airway device 170. For instance, as described herein, a specific key assembly is attached to a specific airway device/mask based on the type of airway device. The key assembly is then attached to system outlet 112 of keying chamber 110. Additionally, as described herein, key assembly further engages its corresponding keyhole and corresponding on/off valve to provide air flow through the correct channel in device 100.

The order of the methods may be changed, and various elements may be added, reordered, combined, omitted, modified, etc. Various modifications and changes may be made as would be obvious to a person skilled in the art having the benefit of this disclosure. The various embodiments described herein are meant to be illustrative and not limiting. Many variations, modifications, additions, and improvements are possible. Accordingly, plural instances may be provided for components described herein as a single instance. Boundaries between various components, operations and data stores are somewhat arbitrary, and particular operations are illustrated in the context of specific illustrative configurations. Other allocations of functionality are envisioned and may fall within the scope of claims that follow. Finally, structures and functionality presented as discrete components in the example configurations may be implemented as a combined structure or component. These and other variations, modifications, additions, and improvements may fall within the scope of embodiments as defined in the claims that follow.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. The words "include", "including", and "includes" mean including, but not limited to. As used throughout this application, the singular forms "a", "an" and "the" include plural referents unless the content clearly indicates otherwise. Thus, for example, reference to "a mask" includes a combination of two or more masks. The term "coupled" means directly or indirectly connected.

What is claimed is:

1. A rescue breath apparatus, comprising:
   a ventilator device configured to be coupled to an air/oxygen source, the ventilator device comprising:
   a first air channel configured to provide a rate and volume of rescue breaths specified for a first patient;
   a second air channel configured to provide a rate and volume of rescue breaths specified for a second patient;
   a third air channel configured to provide a constant flow rate of air/oxygen;
   a system outlet coupled to all of the air channels, the system outlet being configured to output air/oxygen from the device;
   a first keyhole assembly comprising a first valve controlling air flow through the first air channel;
   a second keyhole assembly comprising a second valve controlling air flow through the second air channel; and
   a third keyhole assembly comprising a third valve controlling air flow through the third air channel;
   a first airway device configured to be placed on a face of the first patient;
   a second airway device configured to be placed on a face of the second patient;
   a third airway device configured to provide the constant flow rate of air/oxygen;
   a first key assembly attached to the first airway device, wherein the first key assembly includes a first air tube configured to be coupled to the system outlet and a first key configured to engage the first valve in the first keyhole assembly when the first air tube is coupled to the system outlet;

a second key assembly attached to the second airway device, wherein the second key assembly includes a second air tube configured to be coupled to the system outlet and a second key configured to engage the second valve in the second keyhole assembly when the second air tube is coupled to the system outlet; and a third key assembly attached to the third airway device, wherein the third key assembly includes a third air tube configured to be coupled to the system outlet and a third key configured to engage the third valve in the third keyhole assembly when the third air tube is coupled to the system outlet.

2. The apparatus of claim 1, further comprising:

a fourth air channel configured to provide a rate and volume of rescue breaths specified for a third patient;

a fourth keyhole assembly comprising a fourth valve controlling air flow through the fourth air channel;

a fourth airway device configured to be placed on a face of the third patient; and a fourth key assembly attached to the fourth airway device, wherein the fourth key assembly includes a fourth air tube configured to be coupled to the system outlet and a fourth key configured to engage the fourth valve in the fourth keyhole assembly when the fourth air tube is coupled to the system outlet.

3. The apparatus of claim 2, wherein the first patient is an adult patient, the second patient is a child patient, and the third patient is an infant patient.

4. The apparatus of claim 1, wherein engagement of a key with a valve in a keyhole assembly opens air/oxygen flow through an air channel corresponding to the keyhole assembly.

5. The apparatus of claim 1, wherein a key engages a valve in a keyhole assembly by pushing a button on the valve to open the valve.

6. The apparatus of claim 1, further comprising a manifold dividing a flow of air/oxygen between the first, second, and third air channels in the ventilator device, wherein the manifold is connected to the first, second, and third valves.

7. The apparatus of claim 1, wherein the first and second air channels include a pneumatic timing circuit to provide a pulsed flow of air through the channel.

8. The apparatus of claim 1, wherein the keyhole assemblies include keyholes for receiving the keys from the key assemblies.

9. The apparatus of claim 8, wherein a key assembly has a defined distance between its air tube and its key that determines the keyhole in which said key engages the valve, the keyholes being spaced at different distances from the system outlet.

10. The apparatus of claim 8, wherein the keyholes are spaced at different distances form the system outlet.

11. A rescue breath system, comprising:

a ventilator device configured to be coupled to an air/oxygen source, the ventilator device comprising:

a first air channel configured to provide a rate and volume of rescue breaths specified for an adult patient;

a second air channel configured to provide a rate and volume of rescue breaths specified for a child patient;

a third air channel configured to provide a rate and volume of rescue breaths specified for an infant patient;

a fourth air channel configured to provide a constant flow rate of air/oxygen;

a system outlet coupled to all of the air channels, the system outlet being configured to output air/oxygen from the device;

a first keyhole assembly comprising a first valve controlling air flow through the first air channel;

a second keyhole assembly comprising a second valve controlling air flow through the second air channel;

a third keyhole assembly comprising a third valve controlling air flow through the third air channel; and a fourth keyhole assembly comprising a fourth valve controlling air flow through the fourth air channel;

a first airway device configured to be placed on a face of the adult patient;

a second airway device configured to be placed on a face of the child patient;

a third airway device configured to be placed on a face of the infant patient;

a fourth airway device configured to provide the constant flow rate of air/oxygen;

a first key assembly attached to the first airway device, wherein the first key assembly includes a first air tube configured to be coupled to the system outlet and a first key configured to engage the first valve in the first keyhole assembly when the first air tube is coupled to the system outlet;

a second key assembly attached to the second airway device, wherein the second key assembly includes a second air tube configured to be coupled to the system outlet and a second key configured to engage the second valve in the second keyhole assembly when the second air tube is coupled to the system outlet;

a third key assembly attached to the third airway device, wherein the third key assembly includes a third air tube configured to be coupled to the system outlet and a third key configured to engage the third valve in the third keyhole assembly when the third air tube is coupled to the system outlet; and a fourth key assembly attached to the fourth airway device, wherein the fourth key assembly includes a fourth air tube configured to be coupled to the system outlet and a fourth key configured to engage the fourth valve in the fourth keyhole assembly when the fourth air tube is coupled to the system outlet.

12. The system of claim 11, wherein engagement of a key with a valve in a keyhole assembly opens air/oxygen flow through an air channel corresponding to the keyhole assembly.

13. The system of claim 11, wherein a key engages a valve in a keyhole assembly by pushing a button on the valve to open the valve.

14. The system of claim 11, wherein the first, second, and third air channels include a pneumatic timing circuit to provide a pulsed flow of air through the channel.

15. The system of claim 11, wherein the first, second, and third air channels include pressure regulators to reduce the pressure of air/oxygen flowing through the air channels.

16. The system of claim 11, wherein the fourth air channel includes a needle valve set to provide the constant flow of air/oxygen through the fourth air channel at a predetermined rate.

17. The system of claim 11, wherein the keyhole assemblies include keyholes for receiving the keys from the key assemblies.

18. The system of claim 17, wherein a key assembly has a defined distance between its air tube and its key that determines the keyhole in which said key engages the valve, the keyholes being spaced at different distances from the system outlet.

19. The system of claim 17, wherein the keyholes are spaced at different distances form the system outlet.

20. The system of claim 19, wherein the key assemblies have different distances between their respective air tubes and keys, the distance between an air tube and a key on a key assembly corresponding to the distance from the system outlet of the keyhole associated with the key assembly.

* * * * *